(12) United States Patent
Mizuno et al.

(10) Patent No.: US 9,594,037 B2
(45) Date of Patent: Mar. 14, 2017

(54) ANALYZING APPARATUS AND CALIBRATION METHOD

(71) Applicant: HORIBA, LTD., Kyoto (JP)

(72) Inventors: Yusuke Mizuno, Kyoto (JP); Tomoki Aoyama, Kyoto (JP)

(73) Assignee: Horiba, Ltd., Kyoto (JP)

( * ) Notice: Subject to any disclaimer, the term of this patent is extended or adjusted under 35 U.S.C. 154(b) by 2 days.

(21) Appl. No.: 14/715,812

(22) Filed: May 19, 2015

(65) Prior Publication Data

US 2015/0338357 A1 Nov. 26, 2015

(30) Foreign Application Priority Data

May 20, 2014 (JP) .................................. 2014-104789
May 21, 2014 (JP) .................................. 2014-104790

(51) Int. Cl.
| | |
|---|---|
| *G01N 23/223* | (2006.01) |
| *G01T 7/04* | (2006.01) |
| *G01T 7/00* | (2006.01) |
| *G01N 1/22* | (2006.01) |
| *G01N 15/06* | (2006.01) |

(52) U.S. Cl.
CPC ......... *G01N 23/223* (2013.01); *G01N 1/2205* (2013.01); *G01N 15/0625* (2013.01); *G01T 7/005* (2013.01); *G01T 7/04* (2013.01); *G01N 2223/651* (2013.01)

(58) Field of Classification Search
None
See application file for complete search history.

(56) References Cited

U.S. PATENT DOCUMENTS

| | | | | |
|---|---|---|---|---|
| 2010/0002833 A1* | 1/2010 | Matoba | ................ | G01N 23/223 378/44 |
| 2015/0338534 A1* | 11/2015 | Mizuno | ................ | G01N 23/223 378/45 |

FOREIGN PATENT DOCUMENTS

| | | | | |
|---|---|---|---|---|
| JP | 2008-261712 A | | 10/2008 | |
| JP | 2008261712 A | * | 10/2008 | ............. G01N 15/02 |

OTHER PUBLICATIONS

Shankar Gopala Aggarwal, et al.; Chemical Closure Study on Hygroscopic Properties of Urban Aerosol Particles in Sapporo, Japan; Environmental Science and Technology; pp. 6920-6925; vol. 41, No. 20; 2007.

* cited by examiner

*Primary Examiner* — Michael Logie
(74) *Attorney, Agent, or Firm* — Brooks Kushman P.C.

(57) ABSTRACT

In an analyzing apparatus for analyzing compositions using a fluorescent X-ray in the atmosphere, a calibration to eliminate influences caused by a time-dependent change is performed. The analyzing apparatus includes an emission unit, a detection unit, an environment measurement unit, and a time-dependent change calculation unit. The emission unit emits a primary X-ray. The detection unit detects an intensity of a secondary X-ray passing through the atmosphere. The environment measurement unit measures an environment parameter defining the atmosphere. The time-dependent change calculation unit calculates a time-dependent change of the intensity of the secondary X-ray between a first timing and a second timing, based on a first environment parameter, a first intensity of the secondary X-ray, a second environment parameter, and a second intensity of the secondary X-ray.

3 Claims, 11 Drawing Sheets

_US 9,594,037 B2_

ANALYZING APPARATUS AND CALIBRATION METHOD

CROSS-REFERENCE TO RELATED APPLICATIONS

This application claims priority to Japanese Patent Applications No. 2014-104789 filed on May 20, 2014 and No. 2014-104790 filed on May 21, 2014, the disclosures of which are hereby incorporated in their entirety by reference herein.

TECHNICAL FIELD

The present disclosure relates to an analyzing apparatus for analyzing particulate matter and a calibration method for calibrating the analyzing apparatus.

BACKGROUND

Recently, PM 2.5 existing in the atmosphere, which is floating particulate matter having a diameter less than 2.5 µm, is of a large environmental concern. For this reason, an apparatus for analyzing a concentration of PM 2.5 in the atmosphere and elements included in PM 2.5 has been developed in order to monitor a status of PM 2.5. It is considered that the source of PM 2.5 can be predicted by analyzing elements included in PM 2.5. For example, JP 2008-261712A discloses a measurement apparatus for automatically and continuously analyzing kinds of elements that form floating particulate matter in the atmosphere by using a fluorescence X-ray generated from the particulate matter.

An analyzing apparatus, such as the above-described measurement apparatus, for analyzing compositions of elements using a fluorescent X-ray, includes an X-ray source that generates a primary X-ray, which is emitted to an object to be measured in order to generate the fluorescent X-ray, and a detector that detects the fluorescent X-ray. The X-ray source and the detector change their properties as time elapses. Therefore, in the above-described measurement apparatus, in order to reduce influences on a result of the analysis caused by such a time-dependent change, a calibration of an intensity of an X-ray is performed every time when performing the composition analysis, using a standard specimen such as a specimen for performing a span calibration. As described above, if the calibration of the intensity of the X-ray is performed every time when performing the composition analysis, the influences caused by the time-dependent change (a time degradation, etc.) can be eliminated every time when the calibration is performed.

On the other hand, if the composition analysis of collected particulate matter such as PM 2.5 is continuously performed in the atmosphere, the time-consuming calibration using a standard specimen, etc., cannot be performed. Therefore, if the conventional calibration method of the intensity of the X-ray is used when the analyzing apparatus continuously performs the composition analysis, the composition analysis is influenced by the time-dependent change of the analyzing apparatus.

SUMMARY

Embodiments of the present disclosure calibrate an analyzing apparatus that performs a composition analysis in the atmosphere using a fluorescent X-ray in order to eliminate influences caused by time-dependent changes that depend on elements to be measured.

A plurality of aspects of embodiments to solve the problem will be described below. These aspects can be combined arbitrarily if required. An analyzing apparatus according to one aspect of the present disclosure includes an emission unit, a detection unit, an environment measurement unit, and a time-dependent change calculation unit. The emission unit is configured to emit a primary X-ray in the atmosphere and the primary X-ray excites the particulate matter to generate the fluorescent X-ray. The detection unit is configured to detect a secondary X-ray, which is generated by emitting the primary X-ray and passes through the atmosphere. The environment measurement unit is configured to measure an environment parameter defining the atmosphere. The time-dependent change calculation unit is configured to calculate a time-dependent change or a rate of the time-dependent change between intensities of the secondary X-rays detected at a first timing and at a second timing, based on a first environment parameter, a first intensity of the secondary X-ray, a second environment parameter, and a second intensity of the secondary X-ray. The first timing is the timing after the elapse of a predetermined period of time from the second timing. The first environment parameter is measured at the first timing by the environment measurement unit. The first intensity of the secondary X-ray is an intensity of the secondary X-ray detected at the first timing by the detection unit. The second environment parameter is measured at the second timing by the environment measurement unit. The second intensity of the secondary X-ray is an intensity of the secondary X-ray detected at the second timing by the detection unit. Thus, the calibration, which eliminates the influences caused by the time-dependent changes that depend on elements to be measured, can be performed.

It is acceptable that the analyzing apparatus further includes a collection filter configured to collect the particulate matter. It is acceptable that the first intensity of the secondary X-ray and the second intensity of the secondary X-ray are intensities of scattered X-rays generated by emitting the primary X-ray to a non-collection area of the collection filter. Thus, the intensities of the secondary X-rays can be measured by the detection unit without changing the arrangement of the analyzing apparatus.

A calibration method according to another aspect of the present disclosure is the calibration method of an analyzing apparatus for analyzing compositions of particulate matter based on a fluorescent X-ray generated from the particulate matter. The calibration method comprises steps of measuring a first environment parameter at a first timing, measuring a first intensity of a secondary X-ray at the first timing, measuring a second environment parameter at a second timing, the first timing being the timing after the elapse of a predetermined period of time from the second timing, measuring a second intensity of the secondary X-ray at the second timing, and calculating a time-dependent change or a rate of the time-dependent change between intensities of the secondary X-rays detected at the first timing and at the second timing, based on the first environment parameter, the first intensity of the secondary X-ray, the second environment parameter, and the second intensity of the secondary X-ray. Thus, the calibration, which eliminates the influences caused by the time-dependent changes that depend on elements to be measured, can be performed.

According to the above-described analyzing apparatus for analyzing the compositions using the fluorescent X-ray, the calibration, which eliminates the influences caused by the time-dependent changes that depend on elements to be measured, can be performed.

DETAILED DESCRIPTION

As required, detailed embodiments of the claimed subject matter are disclosed herein; however, it is to be understood that the disclosed embodiments are merely illustrative and may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the claimed subject matter.

1. First Embodiment (1) Overall Structure of an Analyzing Apparatus

Figure 1:
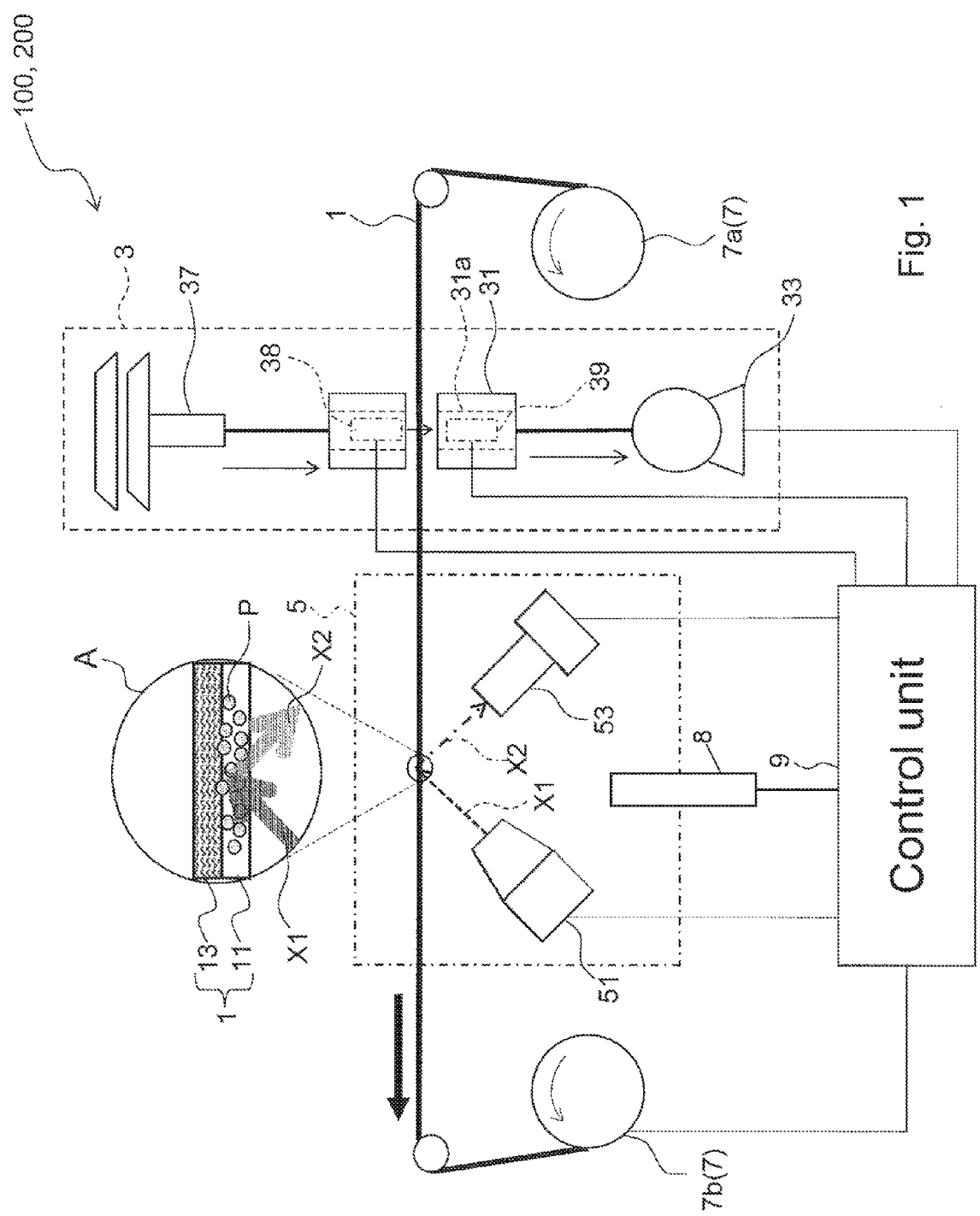
FIG. 1 shows a structure of an analyzing apparatus.

A structure of an analyzing apparatus 100 according to a first embodiment will be described, referring to FIG. 1, which shows a structure of the analyzing apparatus. The analyzing apparatus 100 is the analyzing apparatus that analyzes compositions of particulate matter P (described later) based on a florescent X-ray generated from the particulate matter P by emitting a primary X-ray X1 (described later) to the particulate matter P. The analyzing apparatus 100 includes a collection filter 1, a sampling unit 3, an analysis unit 5, a filter moving unit 7, an environment measurement unit 8, and a control unit 9.

The collection filter 1 collects the particulate matter P included in the atmosphere sampled by the sampling unit 3. Therefore, the collection filter 1 has a collection layer 11 that has pores trapping the particulate matter P. Fluorine-based resin (for example, polytetrafluoroethylene (PTFE)) can be used as the material of the collection layer 11, for example.

The thickness of the collection layer 11 is adjusted such that the absorption of an X-ray, such as the primary X-ray and the fluorescent X-ray, in the collection layer 11 is less than the predetermined level. In the present embodiment, the thickness of the collection layer 11 is 3 to 35 μm. In addition, the collection filter 1 has a reinforcement layer 13 on the main surface of the collection layer 11 to reinforce the collection layer 11. In other words, the collection filter 1 has a double-layer structure having the collection layer 11 and the reinforcement layer 13.

The overall thickness of the collection filter 1 that has the collection layer 11 and the reinforcement layer 13 is between 100 and 200 μm (140 μm, for example) in average in order to adjust the absorption of a X-ray by the collection filter 1 to less than the predetermined level. Materials that pass a gas, include no or little element to be measured, and have sufficient strength are chosen for the reinforcement layer 13. Non-woven fabrics of polyethylene, polypropylene, polyethylene terephthalate (PET), nylon, polyester, and/or polyamide can be used as the material for the reinforcement layer 13. Especially, the non-woven fabric of polypropylene and polyester enables the accurate measurement because such non-woven fabric has sufficient strength and does not include impurities that can be a noise for the fluorescent X-ray analysis.

The sampling unit 3 samples the atmosphere around the analyzing apparatus 100 and sprays the sampled atmosphere onto the collection filter 1. For example, in the sampling unit 3, the atmosphere, which is suctioned from a sampling port 37 by the suction of a suction pump 33, is sprayed onto the collection filter 1 by the suction power of the suction pump 33. It should be noted that a meshed support member that supports the collection filter 1 may be arranged in a first opening 31a (FIG. 1). Thus, the deformation and the damage of the collection filter 1 caused by the suction of the collection filter 1 can be avoided.

The sampling unit 3 includes a β-ray emission unit 38 and a β-ray detection unit 39. A particle mass concentration calculation unit 97 (FIG. 2) of a control unit 9 measures a particle mass concentration of the particulate matter P, which is collected in the collection filter 1. The measurement is performed based on an intensity of a β-ray that is emitted by the β-ray emission unit 38, passes through the collection filter 1 and the particulate matter P, and is detected by the β-ray detection unit 39.

The analysis unit 5 analyzes elements (compositions) included in the particulate matter P. In the present embodiment, the analysis unit 5 analyzes mainly metallic elements included in the particulate matter P. Metallic elements included in the particulate matter P may include sodium, aluminum, calcium, titanium, vanadium, manganese, zinc, lead, barium, antimony, lanthanum, and samarium. In addition, the analysis unit 5 also analyzes elements other than metallic elements such as sulfur, chlorine, bromine, etc.

The filter moving unit 7 moves the collection filter 1 such that the collection filter 1 is moved by forwarding the collection filter 1 from a forwarding reel 7a while winding the collection filter 1 to a winding reel 7b of the filter moving unit 7.

The environment measurement unit 8 includes a thermometer, a barometer, and a hygrometer (not shown in the figure). The environment measurement unit 8 measures the temperature, the pressure, and the humidity of the analysis unit 5 and the area around the analysis unit 5 as an environment parameter to define the atmosphere around the analyzing apparatus 100. The control unit 9 controls the analyzing apparatus 100. The control unit 9 also inputs intensities of the X-ray detected by the detection unit 53 of the analysis unit 5 and performs various operations using the inputted intensities of the X-ray.

(2) Structure of Analysis Unit

Next, the structure of the analysis unit 5 will be described. The analysis unit 5 generates and detects the fluorescent X-ray from the particulate matter P collected by the collection filter 1. Therefore, the analysis unit 5 includes an emission unit 51 and a detection unit 53. It should be noted that the emission unit 51 and the detection unit 53 are not housed in the inner space of a casing, etc. that is separated from the outer atmosphere. Thus, the analysis unit 5 can analyze the compositions of the particulate matter P continuously and at a high speed without controlling the environment of the inner space of the casing, etc.

The emission unit 51 is an X-ray generation apparatus that generates an X-ray by emitting an electron beam to a target (a palladium target, for example). The emission unit 51 is arranged such that it emits a primary X-ray X1 to a measurement area A in the atmosphere. The measurement area A is the area to which the particulate matter P sampled by the sampling unit 3 are sent by the filter moving unit 7 when the analyzing apparatus 100 analyzes elements included in the particulate matter P.

In addition, a primary filter (not shown in the figure) is provided at the exit of the emission unit 51. The primary filter reduces the intensity of the primary X-ray in the wavelength ranges that correspond to the wavelengths of the fluorescent X-ray generated from elements to be measured. Thus, the background component of the X-ray detected by the detection unit 53 can be reduced.

The detection unit 53 detects a secondary X-ray X2 that is generated by emitting the primary X-ray X1 and passes through the atmosphere. For example, a semiconductor detector, such as a silicon semiconductor detector, a silicon drift detector (SDD), etc., can be used as the detection unit 53.

(3) Structure of Control Unit

Figure 2:
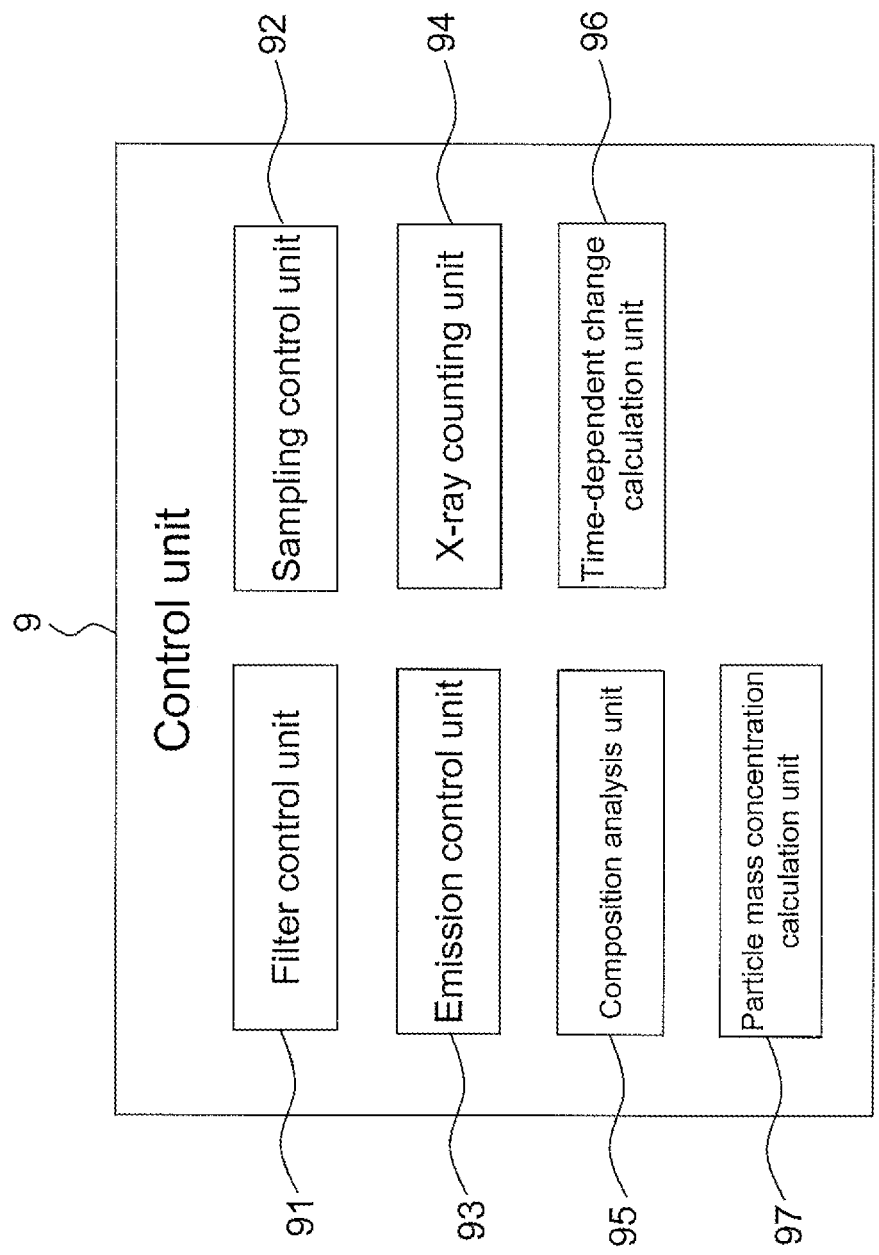
FIG. 2 shows a structure of a control unit of a first embodiment.

Next, the structure of the control unit 9 will be described, referring to FIG. 2, which shows the structure of the control unit. The control unit 9 is a computer system that has a central processing unit (CPU), a storage device such as a read only memory (ROM), a hard drive, etc., a display, and interfaces. The functions of some or all of the elements of the control unit 9 described below may be realized by a program stored in the storage device of the above computer system. In addition, the functions of some or all of the elements of the control unit 9 may be realized by a semiconductor device such as a customized IC.

The control unit 9 includes a filter control unit 91, a sampling control unit 92, an emission control unit 93, an X-ray counting unit 94, a composition analysis unit 95, a time-dependent change calculation unit 96, and the above-described particle mass concentration calculation unit 97. The filter control unit 91, for example, controls the rotation of a motor (not shown in the figure) that controls the rotation of the winding reel 7b. In addition, the filter control unit 91 controls the pushing force of the collection filter 1.

The sampling control unit 92 controls the sampling unit 3, for example, by controlling the suction power of the suction unit 31 and the flow rate of the atmosphere in the sampling unit 3.

The emission control unit 93 adjusts the intensity of the primary X-ray X1. The X-ray counting unit 94 counts the number of the pulse signals from the detection unit 53 within the predetermined signal value range and outputs the counting result. The composition analysis unit 95 calibrates the analysis unit 5 and analyzes compositions (elements) of the particulate matter P. The time-dependent change calculation unit 95 calculates the change of the intensities of the secondary X-ray detected at a first timing (described later) and a second timing (described later).

(4) Operation of Analyzing Apparatus

I. Composition Analysis of Particulate Matter

Figure 3:
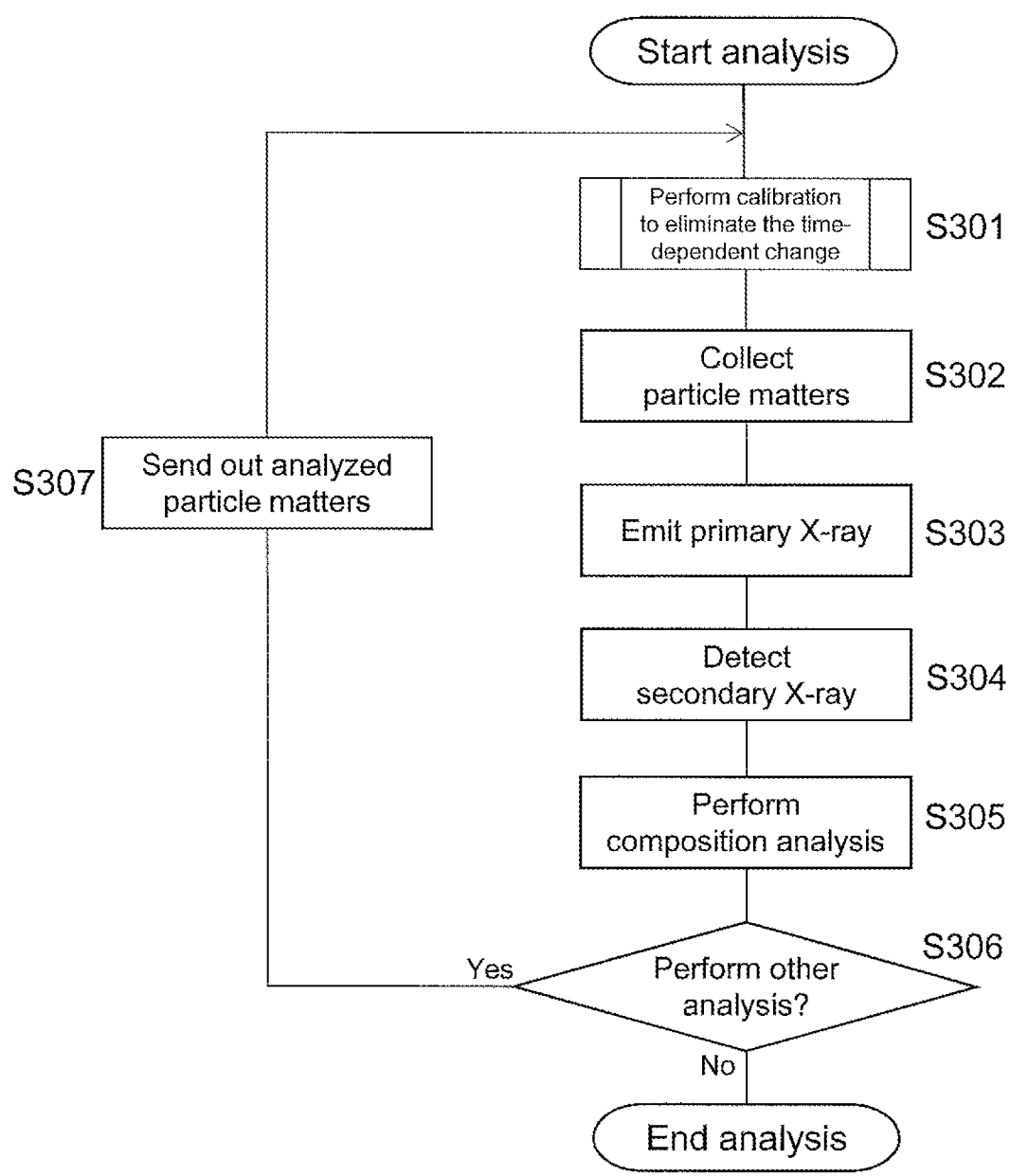
FIG. 3 shows a flowchart of a composition analysis method of particulate matter according to a first embodiment.

The operation of the analyzing apparatus 100 when performing the composition analysis of the particulate matter P will be described below, referring to FIG. 3, which shows a flowchart of the composition analysis method of the particulate matter. Before performing the composition analysis of the particulate matter P described below, the background calibration using the calibration base material made of the material substantially transparent to X-rays such as polycarbonate, and the span calibration using the base material made of, for example, polycarbonate on which the predetermined amount of the standard specimen (preferably the similar material to the particulate matter P to be measured) approved by National Institute of Standards & Technology (NIST) are performed when required.

The measurement results (the X-ray profile of the counting result) of the intensities of the X-ray and the above-described environment parameters obtained when performing the background calibration and/or the span calibration are associated with each other and stored in the storage device of the control unit 9.

After performing the background calibration and the span calibration when required and before the composition analysis, the calibration to eliminate the influences caused by the time-dependent change of the intensity of the X-ray is performed (step S301). In the present embodiment, the calibration to eliminate the influences caused by the time-dependent change is performed for each of the standard curves (described later) for each of the elements to be measured.

After performing the calibration of the intensity of the X-ray to eliminate the influences caused by the time-dependent change, the composition analysis starts. Specifically, the particulate matter P included in the atmosphere are collected to the collection filter 1 by the sampling unit 3, and the collection area of the collection filter 1 in which the particulate matter is collected is moved to the measurement area A by the filter moving unit 7 (step S302). Then, the primary X-ray X1 is emitted to the particulate matter P collected in the collection filter 1 (step S303). Consequently, the fluorescent X-ray having intrinsic energy values depending on the elements included in the particulate matter P is generated from the particulate matter P.

Figure 4:
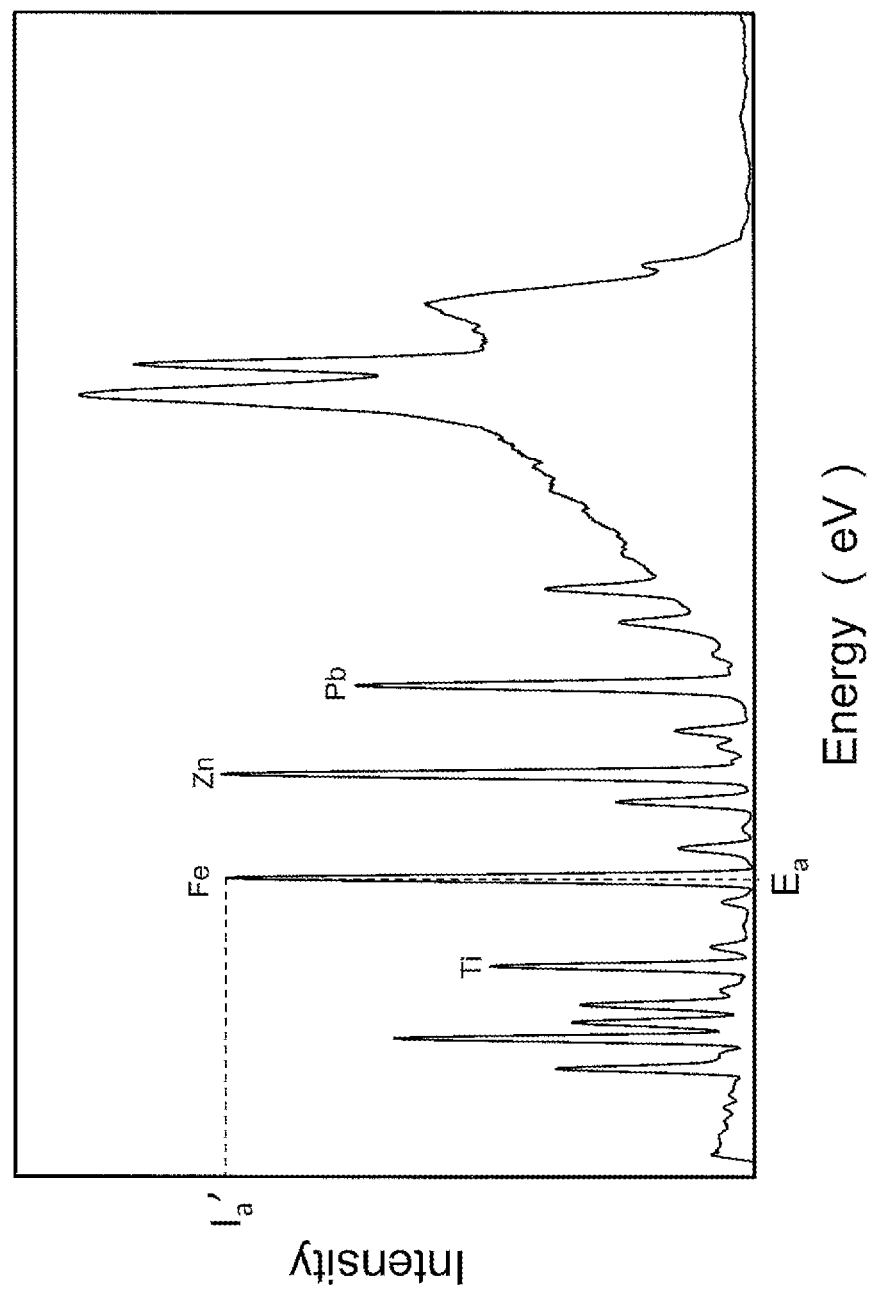
FIG. 4 shows one example of a profile of a counting result that includes a fluorescent X-ray generated from particulate matter.

While the primary X-ray X1 is emitted to the particulate matter P in the collection area, the detection unit 53 detects the secondary X-ray X2 generated from the collection area (step S304). For example, assume that the X-ray profile of the counting result of the secondary X-ray shown in FIG. 4 has been obtained. FIG. 4 shows one example of the profile of the counting result including the fluorescent X-rays from the particulate matter (the X-ray profile).

Next, the composition analysis unit 95 analyzes the composition of the particulate matter P using the above-described X-profile (step S305). Specifically, the intensity of the secondary X-ray at the energy value $E_a$ is first obtained as $I_a'$ from the X-ray profile shown in FIG. 4. Here, it is assumed that $E_a$ is the known energy value at which the fluorescent X-ray of iron (Fe) appears. Then, the intensity of the secondary X-ray $I_a'$ is substituted for Y in the equation $Y=\alpha_{Fe}X+\beta_{Fe}$, which for example expresses the standard curve for iron. The amount of iron included in the particulate matter P can be quantified by reducing the equation $I_a'=\alpha_{Fe}X+\beta_{Fe}$ for X as $(I_a'-\beta_{Fe})/\alpha_{Fe}$.

After performing the composition analysis of the particulate matter P, the composition analysis unit 95 determines whether other analysis is performed or not (step S306). If the composition analysis unit 95 determines that the composition analysis should end ("No" in step S306), the process of the composition analysis in the analyzing apparatus 100 ends. On the other hand, if the composition analysis unit 95 determines that the composition analysis continues ("Yes" in step S306), the particulate matter P that has already been analyzed are sent out from the measurement area A (step S307) and then the process of the composition analysis goes back to step S301. Then, the particulate matter P is collected to the other area of the collection filter 1 and the composition analysis of the particulate matter P collected by the collection filter 1 is performed again.

II. Calibration Method of Intensity of X-Ray to Eliminate Time-Dependent Change

Figure 5:
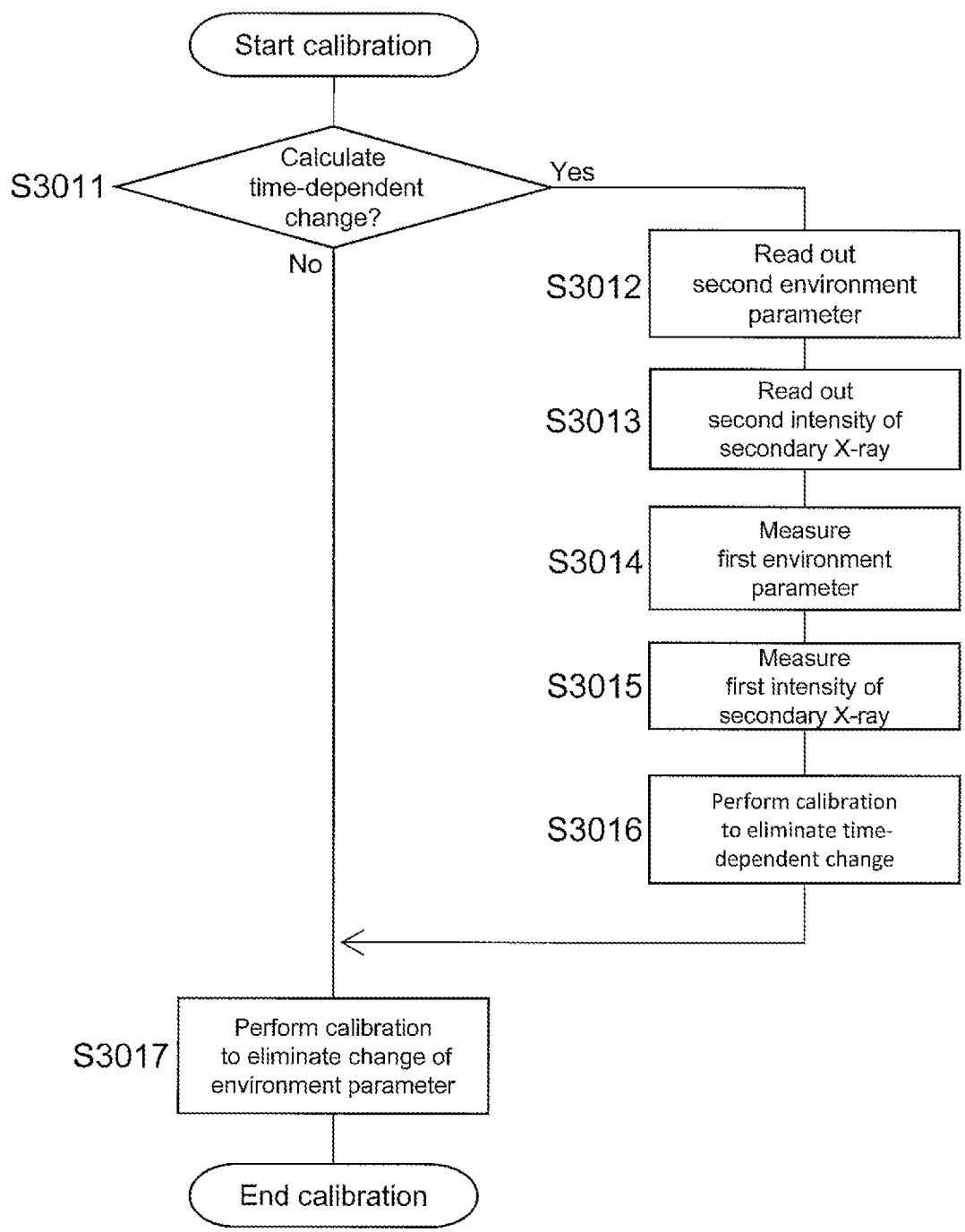
FIG. 5 shows a flowchart of a calibration method of an intensity of an X-ray to eliminate influence of time-dependent change.

Next, the calibration method of the intensity of the X-ray to eliminate the time-dependent change performed in the above step S301 will be described below, referring to FIG. 5, which shows a flowchart illustrating the calibration method of the intensity of the X-ray due to the time-dependent change. When the calibration of the intensity of the X-ray starts, the time-dependent change calculation unit 96 first determines whether the time-dependent change of the intensity of the X-ray of the emission unit 51 and/or the detection unit 53 is calculated or not (step S3011). If the predetermined period (more than one day, for example) has passed since the previous calculation, the time-dependent change calculation unit 96 determines that it is necessary to calculate the time-dependent change of the intensity of the X-ray.

If the time-dependent change calculation unit 96 determines that it is necessary to calculate the time-dependent change of the intensity of the X-ray ("Yes" in step S3011), the process of the calibration proceeds to step S3012. On the other hand, If the time-dependent change calculation unit 96 determines that it is not necessary to calculate the time-dependent change of the intensity of the X-ray ("No" in step S3011), the process of the calibration proceeds to step S3018 to calibrate the intensity of the X-ray to eliminate the influences caused by the change of the environment parameter.

When the calculation of the time-dependent change starts, the time-dependent change calculation unit 96 first reads out the second environment parameter from the storage device of the control unit 9 (step S3012). The second environment parameter may be the environment parameter when the previous background calibration (the span calibration) is performed. In this case, the second timing corresponds to the timing when the previous background calibration (the span calibration) is performed. Alternatively, the environment parameter when the previous calculation of the time-dependent change is performed may be the second environment parameter. In this case, the second timing corresponds to the timing when the previous calculation is performed.

In addition, the time-dependent change calculation unit 96 reads out the second intensity of the secondary X-ray from the storage device (step S3013). If the environment parameter when the previous background calibration is performed is selected as the second environment parameter in step S3012, the time-dependent change calculation unit 96 reads out the background calibration data as the second intensity of the secondary X-ray. On the other hand, if the environment parameter when the previous calculation of the time-dependent change is performed is selected as the second environment parameter, the time-dependent change calculation unit 96 reads out the secondary X-ray data obtained when the precious calculation of the time-dependent change is performed as the second intensity of the secondary X-ray.

Next, the time-dependent change calculation unit 96 inputs the environment parameter at present as the first environment parameter from the environment measurement unit 8 and stores the first environment parameter in the storage device (step S3014).

After measuring the first environment parameter, the primary X-ray X1 is emitted to the non-collection area of the collection filter 1 in which no or little particulate matter is collected. When the primary X-ray is emitted to the non-collection area, a scattered secondary X-ray, which is generated by scattering the primary X-ray on the collection filter 1, is measured as the first intensity of the secondary X-ray by the detection unit 53. As such, the secondary X-ray X2 can be generated without changing the arrangement of the analyzing apparatus 100. Then, the time-dependent change calculation unit 96 calculates the time-dependent change of the intensity of the secondary X-ray (step S3016). Specifically, the time-dependent change or the rate of the time-dependent change is calculated as described below.

First, the first intensity of the secondary X-ray and the second intensity of the secondary X-ray are converted to the intensities of the secondary X-ray, assuming that the environment parameters for the first intensity and the second intensity are the same. For example, the standard intensity of the secondary X-ray obtained when the environment parameter is close to the first environment parameter, and the standard intensity of the secondary X-ray obtained when the environment parameter is close to the second environment parameter, are first selected from the standard intensities of the secondary X-ray measured at various environment parameters in advance. Then, the ratio of the standard intensity of the secondary X-ray obtained when the environment parameter is close to the first environment parameter to that obtained when the environment parameter is close to the second environment parameter is calculated. The change of the intensity of the secondary X-ray caused by the change of the environment parameter can be calibrated such that the second intensity of the secondary X-ray is converted to the intensity of the secondary X-ray measured in the first environment parameter by multiplying the above-described second intensity of the secondary X-ray by the ratio calculated above. In calibrating the change of the intensity of the secondary X-ray, it may be assumed that both the first intensity of the secondary X-ray and the second intensity of the secondary X-ray are measured in other environment parameters other than the first environment parameter.

Then, for each energy value of the fluorescent X-ray of each element to be measured, the ratio of the second intensity of the secondary X-ray after the above calibration to the first intensity of the secondary X-ray is calculated and stored in the storage device as the time-dependent change (the rate of the time-dependent change) of the intensity of the secondary X-ray, for example.

After calculating the above time-dependent change of the intensity of the secondary X-ray, or reading out the time-dependent change stored in the storage device, the composition analysis unit 95 calibrates the above time-dependent change to eliminate the influences caused by the change of the environment parameter (step S3017). If the above time-dependent change of the intensity of the secondary X-ray is calculated at a fourth timing (when a fourth environment parameter is measured), for example, the above time-dependent change is calibrated such that the time-dependent change at the fourth timing is converted to the time-dependent change calculated at present (the first timing). Specifically, the ratio of the standard intensity of the secondary X-ray obtained in the environment parameter close to the first environment parameter, to the standard intensity of the secondary X-ray obtained in the environment parameter close to the fourth environment parameter is first calculated. Then, the time-dependent change in the first environment parameter (when the composition analysis is performed) is calculated by multiplying the time-dependent change at the fourth timing by the above ratio.

Figure 6:
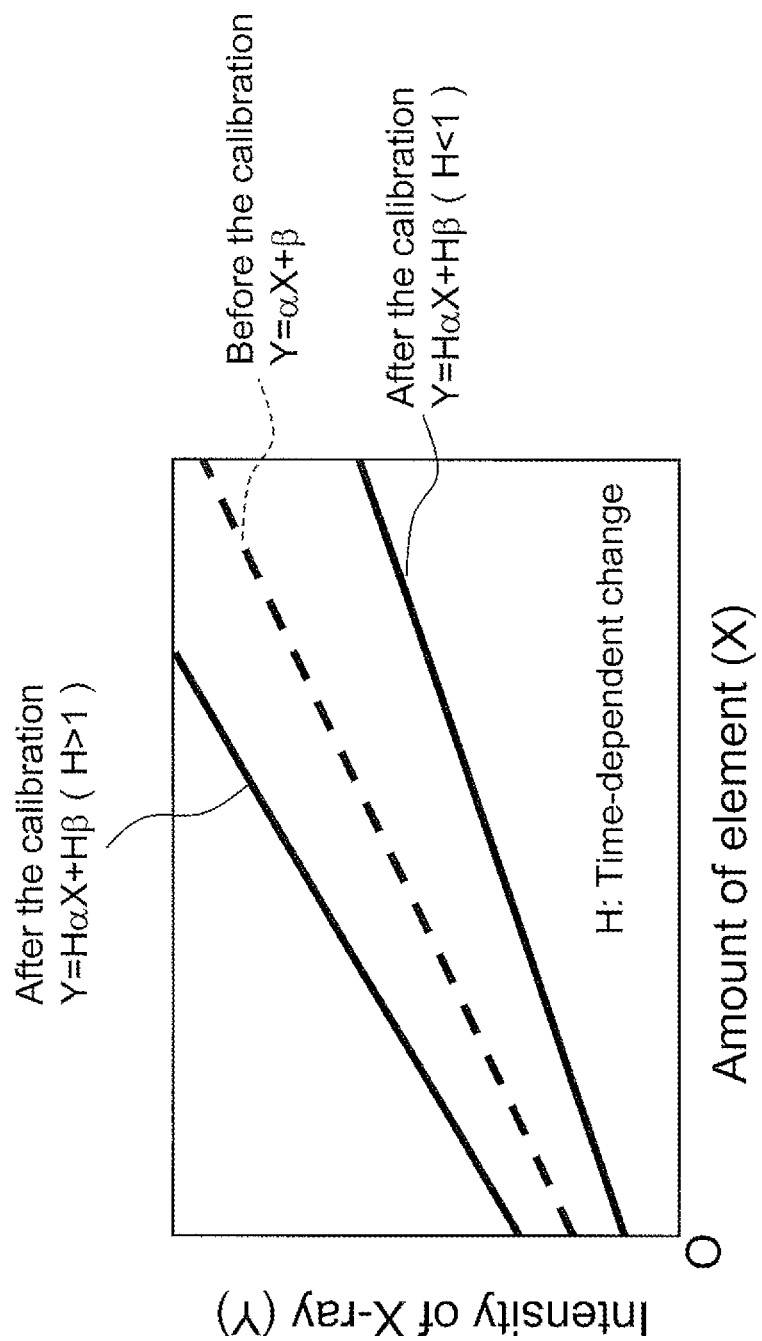
FIG. 6 shows one example of a standard curve after the calibration.

Then, the composition analysis unit 95 calibrates the standard curves to eliminate the influences caused by the time-dependent change and the change of the environment parameter, by multiplying each standard curve of each element to be measured, which is stored in the storage device, by each time-dependent change of the intensity of the secondary X-ray for each element to be measured. For example, assuming that the environment parameters are the same, if the above change is larger than 1, the slope of the standard curve after the calibration is larger than that of the standard curve before the calibration. On the other hand, if the above change is smaller than 1, the slope of the standard curve after the calibration is smaller than that of the standard curve before the calibration, as shown in FIG. 6. In other words, the standard curves change in accordance with the change of the time-dependent change. FIG. 6 shows one example of the standard curve after the calibration.

As described above, the calibration to eliminate the influences caused by the time-dependent change that depends on elements to be measured can be performed by calculating the time-dependent change of the secondary X-ray.

2. Second Embodiment

Figure 7:
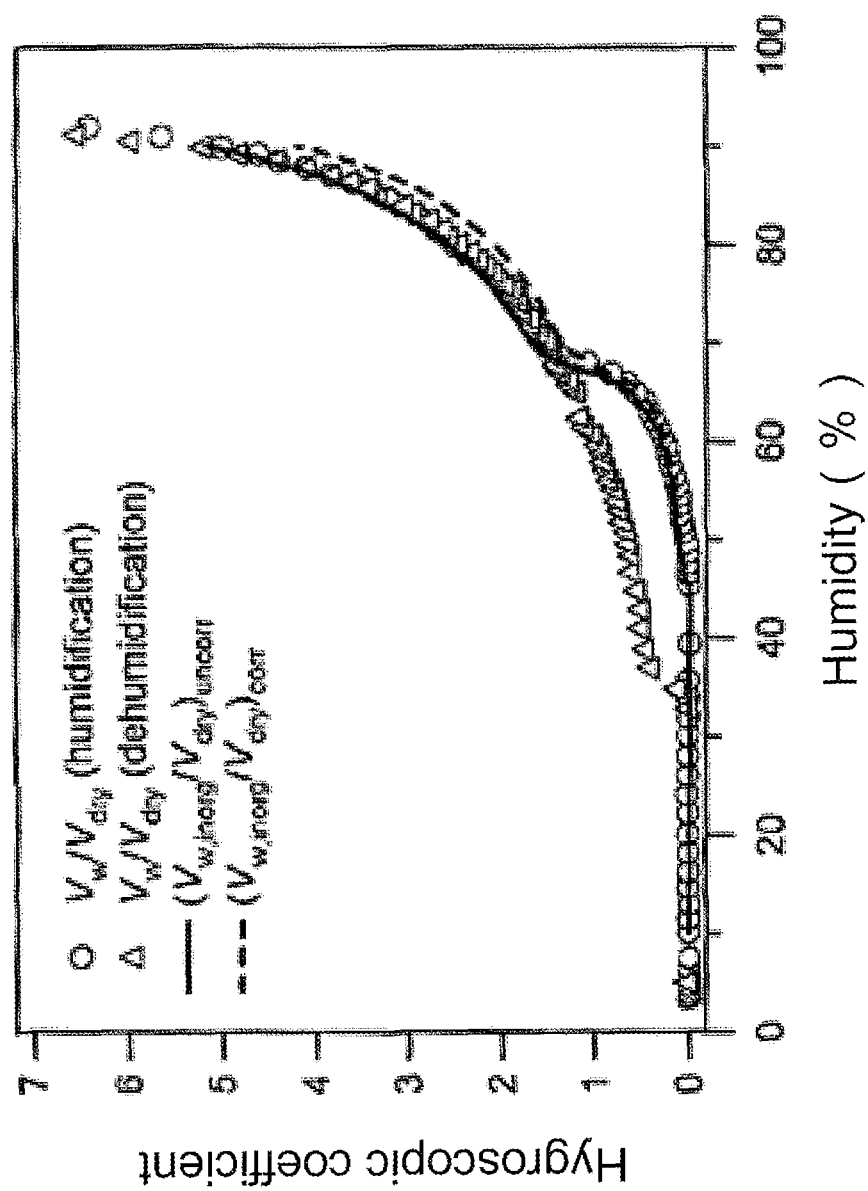
FIG. 7 shows a relationship between a humidity and a hygroscopic coefficient.

In the above-described first embodiment, the calibration (of the standard curves) to eliminate the influences caused by the time-dependent change is performed. The calibrations to eliminate other influences may be performed in order to analyze more accurately the compositions using the fluorescent X-ray generated from the particulate matter P such as PM 2.5. The particle state of the particulate matter included in the atmosphere changes with the environment of the atmosphere such as humidity. For example, as shown in FIG. 7, which is the graph showing the relationship between humidity and hygroscopic coefficient disclosed in Aggarwal et al. (S. G. Aggarwal, et al., "Chemical Closure Study on Hygroscopic Properties of Urban Aerosol Particles in Sapporo, Japan", *Environmental Science and Technology*, p. 6920-6925, 41(20) (2007)), the particle size of the particulate matter is increased, depending on the composition of the particulate matter, in the atmosphere with higher humidity because the particulate matter absorbs moisture. In addition, there may be some fluctuations of the hygroscopic coefficient between the increase of humidity and the decrease of humidity. FIG. 7 shows the relationship between the humidity and the hygroscopic coefficient. In the second embodiment, the calibration to eliminate the above-described influence of the atmosphere on the particle state of the particulate matter is performed.

Figure 8:
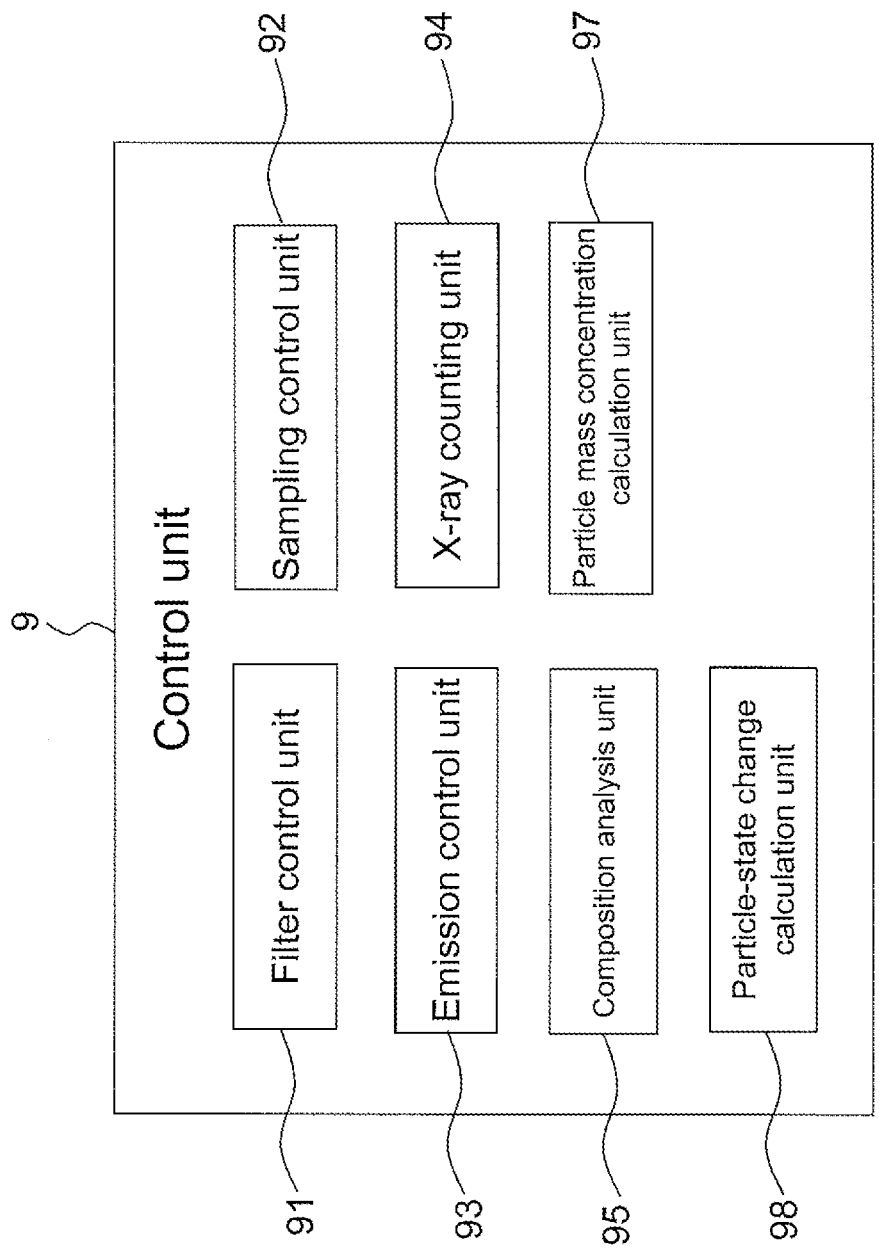
FIG. 8 shows a structure of a control unit according to a second embodiment.
Figure 9:
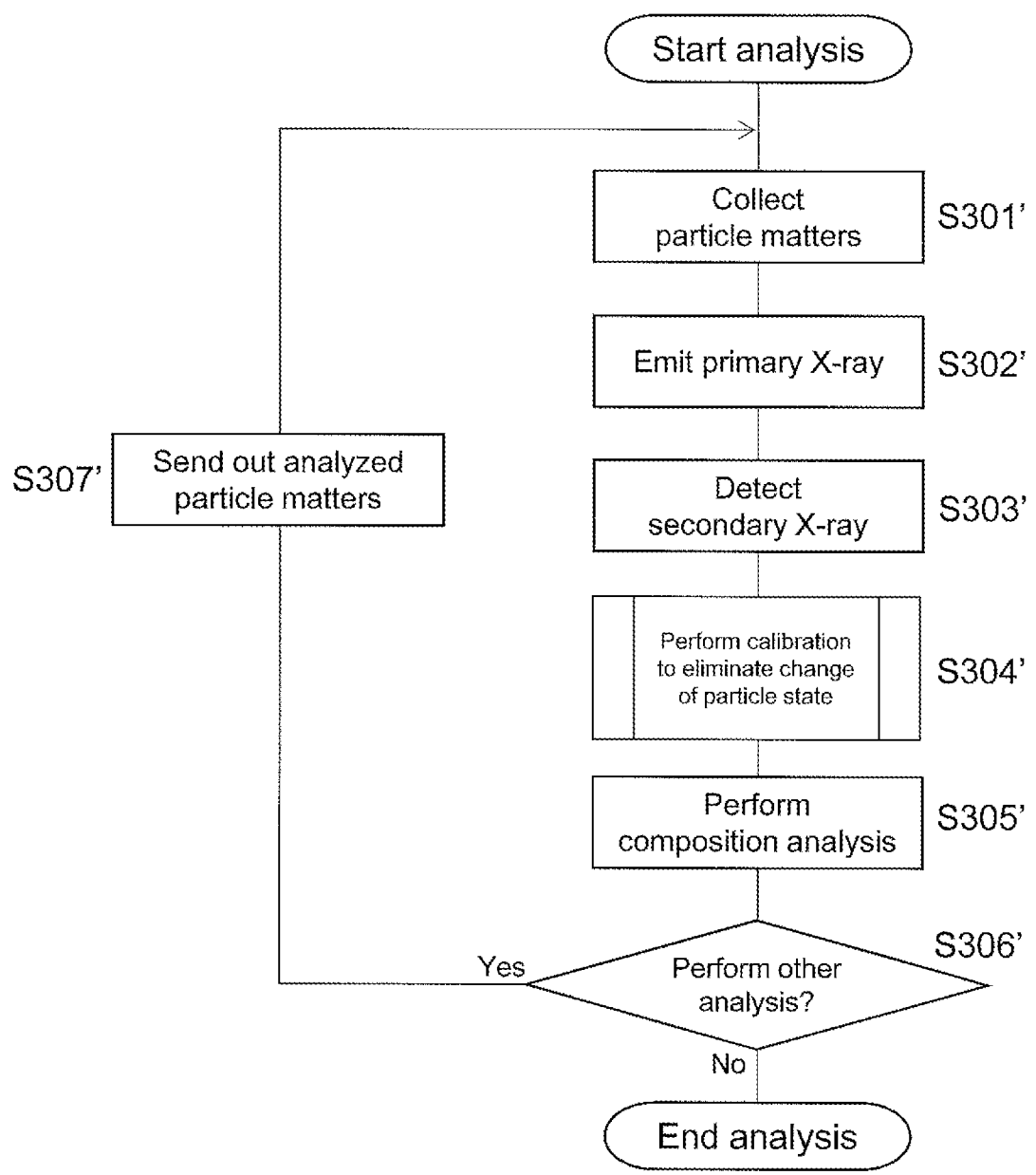
FIG. 9 shows a flowchart of a composition analysis method of particulate matter according to a second embodiment.

An analyzing apparatus 200 according to a second embodiment will be described below. The analyzing apparatus 200 according to the second embodiment (see FIG. 1) has the same structure as the analyzing apparatus 100 according to a first embodiment, except that a control unit 9' of the analyzing apparatus 200 does not have the time-dependent change calculation unit 96, but it has a particle-state change calculation unit 98. The particle-state change unit 98 is configured to calculate a change or a rate of the change of the intensity of the secondary X-ray caused by the change of the particle state of the particulate matter P, as shown in FIG. 8, which shows the structure of the control unit according to a second embodiment. Therefore, the explanations of other elements of the analyzing apparatus 200 according to the second embodiment are omitted. The operation of the composition analysis of the particulate matter P in the analyzing apparatus according to the second embodiment will be described below, referring to FIG. 9. FIG. 9 shows the flowchart of the composition analysis method of particulate matter according to the second embodiment.

Figure 10:
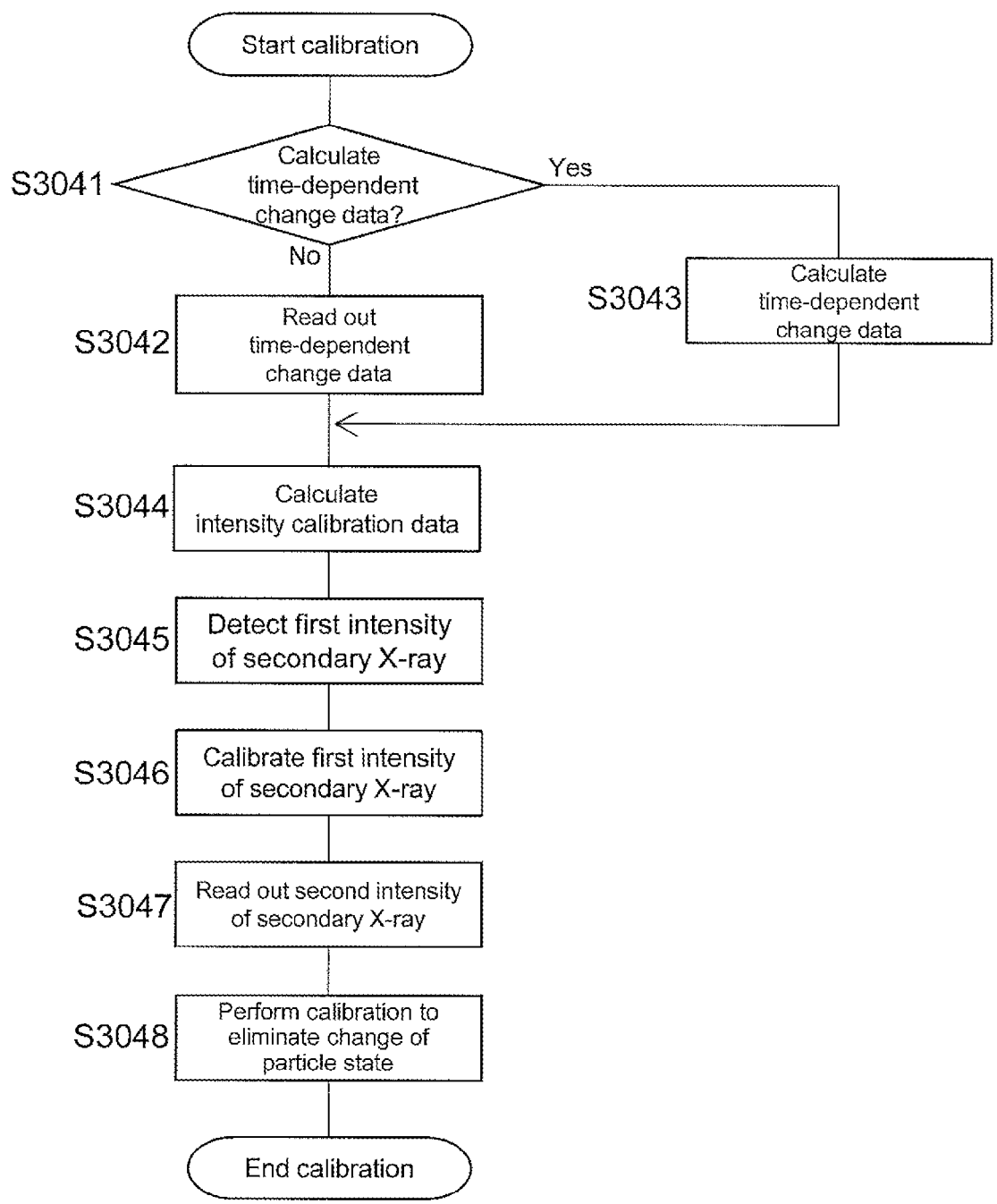
FIG. 10 shows a flowchart of a calibration method to eliminate influences caused by a change of a particle state.

In the flowchart shown in FIG. 9, the calibration to eliminate the influence caused by the change of the particle state of the particulate matter P is performed in the step S304' which is after the step S303' of FIG. 9, in which the secondary X-ray X2 generated from the particulate matter (the collection area) is detected, and before the step S305' in which the composition analysis of the particulate matter P is performed. It should be noted that the operations of the analyzing apparatus 200 in the steps S301' through S303' and S305' through S307' of FIG. 9 correspond to those in the steps S302 through S304 and S305 through S307, respectively. Therefore, only the calibration to eliminate the influences caused by the change of the particle state performed in the step S304' will be described, referring to FIG. 10. FIG. 10 shows the flowchart of the calibration method to eliminate the influences caused by the change of the particle state.

When the calibration to eliminate the influences caused by the change of the particle state starts, the control unit 9' first determines whether it is necessary to calculate time-dependent change data (described later) or not (step S3041). For example, the control unit 9' determines that the time-dependent change data is calculated if more than one day has been passed since the previous calculation of the time-dependent change data. Alternatively, the control unit 9' may determine that the time-dependent data is calculated in every composition analysis.

If the control unit 9' determines that it is necessary to calculate the time-dependent change data ("Yes" in step S3041), the process proceeds to step S3043 to calculate the time-dependent change data. On the other hand, if the control unit 9' determines that it is not necessary to calculate the time-dependent change data ("No" in step S3041), the time-dependent change data stored in the storage device at present is read out from the storage device (step S3042).

In the step S3043, the time-dependent change data is calculated as described below, as the time-dependent change of the intensity of the X-ray generated between the span calibration (corresponding to the second timing) and the present time (corresponding to the first timing). First, the standard intensity of the X-ray is read out from the storage device. For example, the background calibration data obtained (measured) when the background calibration is performed is read out as the standard intensity of the X-ray. Next, the non-collection area of the collection filter 1 is moved to the measurement area A and then the primary X-ray X1 is emitted to the non-collection area. The scattered X-ray data is obtained by detecting the scattered X-ray generated by emitting the primary X-ray X1 to the non-collection area, using the detection unit 53.

Next, for each element to be measured (in other words, each energy value of the fluorescent X-ray generated from each element to be measured), the ratio of the standard X-ray profile, which is the profile of the intensity of the X-ray obtained in the environment parameter close to the environment parameter when performing the span calibration, to a present X-ray profile, which is the profile of the intensity of the X-ray obtained in the environment parameter close to the present first environment parameter, is calculated. Then, for each element to be measured, the ratio of an after-calibration data calculated by multiplying the scattered X-ray data by the ratio calculated above, to the background calibration data is calculated as the time-dependent change data and stored in the storage device.

After calculating or reading out the time-dependent change data, the intensity calibration data is calculated (step S3044). Specifically, the intensity calibration data at the standard timing (when performing the span calibration) to eliminate the influences caused by both the time-dependent change and the change of the environment parameters is calculated by multiplying the ratio of the standard X-ray profile to the present X-ray profile by the above time-dependent change data.

By calculating the time-dependent change data separately when it is necessary, the number of the measurements of the intensity of the X-ray (the scattered X-ray) to calculate the intensity calibration data can be reduced.

Next, a span calibration base material SS is provided in the area other than the measurement area A where the primary X-ray X1 can be emitted and the X-ray generated from a calibration specimen CS supported on the span calibration base material SS can be detected by the detection unit 53. For example, the span calibration base material SS can be provided in the area under the measurement area A of the collection filter 1. In this case, a shielding plate may be provided between the span calibration base material SS and the collection filter 1 in order to prevent the primary X-ray X1 from passing through the span calibration base material SS and reaching the collection filter 1. By providing the span calibration base material SS in the area other than the measurement area A, the secondary X-ray X2 can be obtained while the particulate matter P is collected to the collection filter 1.

If the emission unit 51 emits the primary X-ray X1 after the above step, the detection unit 53 detects the intensity of the secondary X-ray X2 generated from the calibration specimen CS as the first intensity of the secondary X-ray (step S3045). Here, since the span calibration base material SS is provided in the area other than the measurement area A, the intensity of the secondary X-ray obtained as described above is calibrated to eliminate the influences caused by the difference of the distance. For example, the obtained intensity of the secondary X-ray is multiplied by the value $\exp(-\mu^*(d-d'))$, where $\mu$ is the damping constant of the X-ray, d is the path length of the X-ray between the emission unit 51 and the detection unit 53 assuming that the span calibration base material SS is provided in the measurement area A, and d' is the path length of the X-ray between the emission unit 51 and the detection unit 53 assuming that the span calibration base material SS is provided in the area other than the measurement area A. Alternatively, the ratio of the intensity of the secondary X-ray X2 detected when the primary X-ray X1 is emitted to the measurement area A, to the intensity of the secondary X-ray X2 detected when the primary X-ray X2 is emitted to the are other than the measurement area A where the span calibration base material SS is provided may be calculated and stored in advance, and the calibration to eliminate the influences of the distance may be performed using the above ratio.

After detecting the first intensity of the secondary X-ray, the calibration of the intensity of the X-ray, whose standard timing is the timing when performing the span calibration, is performed to the first intensity of the secondary X-ray by multiplying the first intensity of the secondary X-ray by the above-described intensity calibration data (step S3046).

Next, the span calibration data stored in the storage device is read out as the second intensity of the secondary X-ray (step S3047). After reading out the second intensity of the secondary X-ray, the particle-state change calculation unit 98 performs the calibration to eliminate the influences caused by the change of the particle state of the particulate matter P for each element to be measured, based on the difference between the first intensity of the secondary X-ray after the above calibration and the second intensity of the secondary X-ray (step S3048). This is because the influences of the change of the particle state on the fluorescent X-ray are different between elements to be measured.

Figure 11:
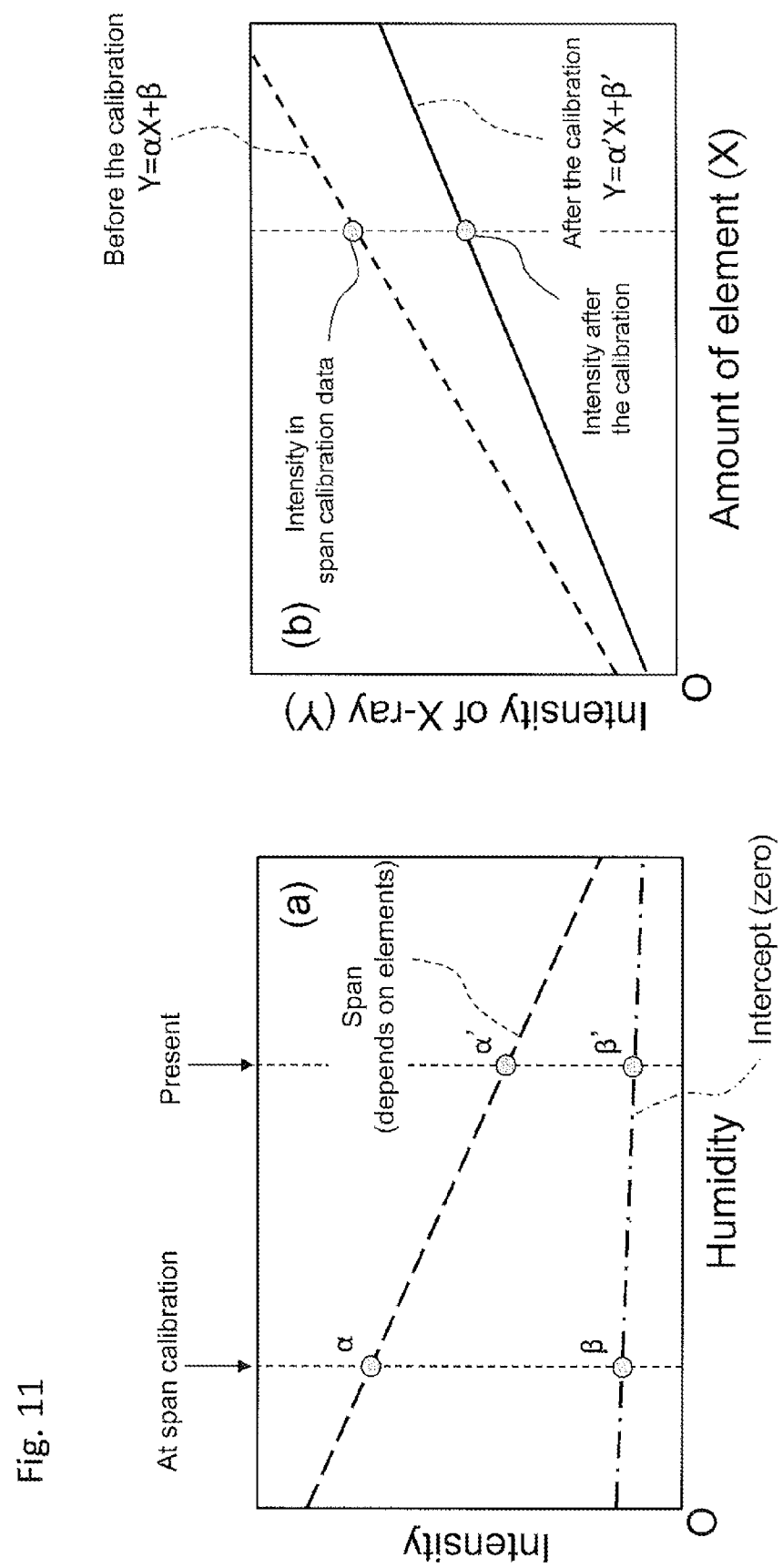
FIG. 11 shows schematically a calibration method to eliminate influences caused by a change of a particle state.

Specifically, using the equations as shown in (a) of FIG. 11 showing the relationships between the slope of the standard curve for each element to be measured and the particle state (the change of the particle state due to the humidity) and between the intercept of the standard curve and the particle state, the slope ($\alpha$) and the intercept ($\beta$) of the standard curve calculated when performing the span calibration are calibrated to $\alpha'$ and $\beta'$, respectively, such that the first intensity of the secondary X-ray after the calibration is on the standard curve as shown in (b) of FIG. 11. FIG. 11 shows schematically the calibration method to eliminate the influences caused by the change of the particle state.

As described above, the calibration of the standard curve to eliminate the influences caused by the change of the particle state for each element to be measured enables the accurate composition analysis even if the particle state of the particulate matter P is changed. It should be noted that the calibration at other standard timings than the second timing (the timing when performing the span calibration) can also be performed.

3. Summary of Second Embodiment

The second embodiment can be summarized as follows. An analyzing apparatus according to the second embodiment is the analyzing apparatus for analyzing compositions of particulate matter based on a fluorescent X-ray generated from the particulate matter. The analyzing apparatus includes an emission unit, a detection unit, and a particle-state change calculation unit. The emission unit is configured to emit a primary X-ray in the atmosphere. The primary X-ray excites the particulate matter to generate the fluorescent X-ray. The detection unit is configured to detect an intensity of a secondary X-ray. The secondary X-ray is the X-ray that is generated by emitting the primary X-ray and passes through the atmosphere. The particle-state change calculation unit is configured to calculate the change or the rate of the change of intensity of the secondary X-ray caused by the change of the particle state of the particulate matter, based on a first intensity of the secondary X-ray and a second intensity of the secondary X-ray. The first intensity of the secondary X-ray is the intensity of the secondary X-ray that is generated by emitting the primary X-ray to a calibration specimen and detected by the detection unit at a first timing. The second intensity of the secondary X-ray is the intensity of the secondary X-ray that is generated by emitting the primary X-ray to a calibration specimen and detected by the detection unit at a second timing.

It is accepted that the analyzing apparatus further includes an environment measurement unit configured to measure an environment parameter defining the atmosphere. In this case, the particle-state change calculation unit calculates the change or the rate of the change of the intensity of the secondary X-ray, based on a first environment parameter measured by the environment measurement unit at the first timing and a second environment parameter measured by the environment measurement unit at the second timing.

A calibration method according to the second embodiment is the calibration method of an analyzing apparatus for analyzing compositions of particulate matter based on a fluorescent X-ray generated from the particulate matter. The calibration method includes measuring a first intensity of a secondary X-ray detected by emitting a primary X-ray to a calibration specimen at a first timing, measuring a second intensity of the secondary X-ray detected by emitting the primary X-ray to the calibration specimen at a second timing, and calculating the change or the rate of the change of the intensity of the secondary X-ray caused by the change of the particle state of the particulate matter, based on the first intensity of the secondary X-ray and the second intensity of the secondary X-ray.

4. Other Embodiments

Some embodiments of the present disclosure have been described above. However, the present disclosure is not limited to the above-described embodiments and various modifications can be made in the scope of the present disclosure. For example, the combinations of the above-described first embodiment and the above-described second embodiment are possible. For example, the control unit 9 of the first embodiment as shown in FIG. 2 may include the particle-state change calculation unit 98 of the second embodiment and the calibration to eliminate the influences caused by the change of the particle state of the particulate matter shown in the steps S3401 through S3408 may be performed after the detection of the secondary X-ray in the step S304 of the first embodiment and before the composition analysis in the step S305 of the first embodiment.

(A) Other Embodiment of Use of Time-Dependent Change

In the above first and second embodiments, if the above-described time-dependent change is less than the predetermined value, the analyzing apparatus may determine that the sensitivity of the X-ray is lowered due to the degradation of the emission unit 51 and/or the detection unit 53. On the other hand, if the above-described time-dependent change is extremely large, it may be determined that the malfunctions of the emission unit 51 and/or the detection unit 53 occur.

(B) Calibration of Peak Shifts

In the above-described first and second embodiments, the peak shifts in the counting result may be calibrated by adjusting the span and/or the zero of the detection unit such that the peaks in the counting result of the scattered X-ray generated by scattering the primary X-ray X1 on the collection filter 1 fit with the peaks having known and unchanged energy values that should be included in the scattered X-ray.

The present disclosure can be widely applied to the analyzing apparatus for analyzing particulate matter.

While representative embodiments are described above, it is not intended that these embodiments describe all possible forms of the disclosure. The words used in the specification are words of description rather than limitation, and it is understood that various changes may be made without departing from the spirit and scope of the disclosure. Additionally, the features of various implementing embodiments may be combined to form further embodiments of the disclosure that are not explicitly described or illustrated.

What is claimed is:

1. An analyzing apparatus for analyzing compositions of particulate matter based on a fluorescent X-ray generated from the particulate matter, the analyzing apparatus comprising:
   an emission unit configured to emit a primary X-ray in the atmosphere, the primary X-ray exciting the particulate matter to generate the fluorescent X-ray;
   a detection unit configured to detect a secondary X-ray generated by emitting the primary X-ray and passing through the atmosphere;
   an environment measurement unit configured to measure an environment parameter comprising at least one of temperature, pressure, and humidity defining the atmosphere; and
   a time-dependent change calculation unit configured to calculate a time-dependent change or a rate of the time-dependent change between intensities of the secondary X-rays detected at a first timing and at a second timing, based on a first environment parameter, a first intensity of the secondary X-ray, a second environment parameter, and a second intensity of the secondary X-ray, wherein
   the first timing is the timing after the elapse of a predetermined period from the second timing, the first environment parameter is measured at the first timing by the environment measurement unit, the first intensity of the secondary X-ray is an intensity of the secondary X-ray detected at the first timing by the detection unit, the second environment parameter is measured at the second timing by the environment measurement unit, and the second intensity of the secondary X-ray is an intensity of the secondary X-ray detected at the second timing by the detection unit.

2. The analyzing apparatus according to claim 1, further comprising a collection filter configured to collect the particulate matter, and wherein the first intensity of the secondary X-ray and the second intensity of the secondary X-ray are intensities of scattered X-rays generated by emitting the primary X-ray to a non-collection area of the collection filter.

3. A calibration method of an analyzing apparatus for analyzing compositions of particulate matter based on a fluorescent X-ray generated by emitting a primary X-ray to the particulate matter, the calibration method comprising:
   measuring a first environment parameter comprising at least one of temperature, pressure, and humidity at a first timing;
   measuring a first intensity of a secondary X-ray at the first timing;
   measuring a second environment parameter comprising at least one of temperature, pressure, and humidity at a second timing, the first timing being the timing after the elapse of a predetermined period from the second timing;
   measuring a second intensity of the secondary X-ray at the second timing; and
   calculating a time-dependent change or a rate of the time-dependent change between intensities of the secondary X-rays detected at the first timing and at the second timing, based on the first environment parameter, the first intensity of the secondary X-ray, the second environment parameter, and the second intensity of the secondary X-ray.

\* \* \* \* \*